United States Patent [19]

Sternberg

[11] 3,933,593
[45] Jan. 20, 1976

[54] RATE SENSING BATCH ANALYSIS METHOD

[75] Inventor: James C. Sternberg, Fullerton, Calif.

[73] Assignee: Beckman Instruments, Inc., Fullerton, Calif.

[22] Filed: Aug. 9, 1972

[21] Appl. No.: 279,011

Related U.S. Application Data

[62] Division of Ser. No. 117,632, Feb. 22, 1971, abandoned, which is a division of Ser. No. 618,859, Feb. 27, 1967.

[52] U.S. Cl. ....... 195/103.5 R; 23/230 R; 23/230 B; 128/2 E; 128/2 G; 195/103.5 C; 324/30 R
[51] Int. Cl. ........................................... G01h 31/14
[58] Field of Search ............. 204/1 T, 195 P, 195 B; 195/103.5 R, 103.5 C; 128/2 E, 2 G; 23/230 R, 230 B

[56] References Cited
UNITED STATES PATENTS

| | | |
|---|---|---|
| 3,123,443 | 3/1964 | Smeby .................... 195/103.5 X |
| 3,227,643 | 1/1966 | Okun et al .................... 204/195 P |
| 3,278,408 | 10/1966 | Leonard et al. .............. 204/195 P |
| 3,367,849 | 2/1968 | Blaedel et al. .................... 204/1 T |
| 3,404,069 | 10/1968 | Ware ............................. 195/103.5 |
| 3,421,982 | 1/1969 | Schultz et al. ............... 195/103.5 |

OTHER PUBLICATIONS

Leland C. Clark, Jr. et al., Annals of the New York Academy of Sciences, V. 102, Art. 1, pp. 29–44 (1962).
H. V. Malmstadt et al., "Electronics for Scientists", pp. 358, 359, 394 & 395 (1963).
D. Keilin et al., Biochem. J., V. 42, pp. 230–238, (1948).

Primary Examiner—G. L. Kaplan
Attorney, Agent, or Firm—R. J. Steinmeyer; R. R. Meads

[57] ABSTRACT

A portable, automated chemical analyzer having a polarographic oxygen electrode submerged in a batch of stirred solution. The signal from the electrode is directly differentiated and amplified to produce a signal proportional to the time rate of change of oxygen concentration. The membrane of the polarographic sensor is stretched very tightly over the cathode surface to provide a high signal-to-noise ratio. Methods for analyzing glucose-glucose oxidase, catalase-$H_2O_2$ and various other enzyme systems by the polarographic electrode oxygen sensing apparatus include the steps of converting the sensed signal into time rate of change of oxygen concentration and recording the maximum rate of change of oxygen concentration.

46 Claims, 10 Drawing Figures

RATE SENSING BATCH ANALYSIS METHOD

CROSS-REFERENCE TO RELATED APPLICATION

This is a division of my copending application Ser. No. 117,632 filed Feb. 22, 1971, now abandoned, entitled "RATE SENSING BATCH ANALYSIS AND ENZYME USED THEREIN," which is a division of my original application Ser. No. 618,859, filed Feb. 27, 1967, entitled "RATE SENSING BATCH ANALYZER."

BACKGROUND OF THE INVENTION

1. Field of the Invention

The present invention relates to a portable automated chemical analyzing apparatus and to methods of utilizing the apparatus especially in the kinetic determination of enzyme activity and concentration of substances reactive with enzymes.

The batch analyzer of the invention provides a most convenient instrument for rapidly determining quantitative information concerning a series of chemical and especially biological samples. A series of samples of known volume can be prepared, and each analyzed in sequence and removed from the apparatus within a very short interval with ready interspacing of calibration samples.

The instrument is rapidly set up and put into operation, makes the determinations rapidly and accurately, uses a small sample size and measures true concentration. The batch analyzer of the invention does not require more than minimum dexterity to operate, is stable over extended periods and since it is fairly inexpensive and gives an individual result rapidly and conveniently, more analyses are apt to be run.

The apparatus of the invention relies on the measurement of true instantaneous rate at very early stages of the reaction before much reactant is consumed and even with gaseous reactants the reactions can be open to the atmosphere since the indicative data is collected before back diffusion of gas into the solution can influence the results.

The recorded rate sensing signal results in a sharply defined peak corresponding to apparent maximum rate which is directly proportional to initial concentration, eliminating necessity to extrapolate to true initial conditions to determine concentration.

The apparent maximum rate is obtained in a relatively short time interval of the order of 10 seconds to 10 minutes, saving analysis time, thus permitting more samples to be run in the same time interval. Direct rate sensing with the instrument of the invention is further applicable both to concentration and activity determinations and to very low levels of concentration determinations including even those previously considered trace level since they could not be effectively monitored with prior art apparatus and methods.

With reference to the enzymatic assay of glucose in blood and urine by oxidation of glucose with glucose-oxidase enzyme, to produce hydrogen peroxide and gluconic acid, a presently available automated analyzer relies on the spectrophotometric response of the color reaction between hydrogen peroxide, peroxidase and a chromogen. The strong oxidizing agent, hydrogen peroxide can react with other reducible substances and other impurities interfere with the peroxide-peroxidase system causing loss in specificity and accuracy. The assay cannot be conducted without deproteinization of blood samples or pre-purification of the urine samples and even with preliminary purification, assay of urine glucose below the trace 100 mg percent level is not possible.

The batch analyzer of the invention is applied to the direct monitoring of oxygen consumed in the glucose oxidase-glucose reaction does not require preliminary purification or deproteinization of blood or urine samples, gives highly accurate results on an absolute basis and is insensitive to many impurities considered to interfere with many other analytical procedures.

The specificity and sensitivity of the analyzer of the invention in the very low ranges of glucose provides new means of identifying traumatic conditions such as diabetes at earlier stages. The ability to effectively monitor catalase activity also broadens the range of diagnostic tools available to the physician especially in recognizing the diseased states of the central nervous system.

SUMMARY OF THE INVENTION

Briefly, the instrumentation of the invention includes a sample vessel, sensor means for forming an electrical signal proportional to concentration of a substance reacting within the vessel and having a high signal to noise ratio, electrical means for directly differentiating the signal into a time rate of change signal, and means for recording the maximum rate signal.

In the analysis of blood or urine glucose, equal volume portions of blood or urine samples are added either successively to a single batch of buffered glucose oxidase (G.O.) solution or to successive samples of equal quantities of G.O. solution of the same activity. The solution is stirred and reaction proceeds in the presence of an oxygen sensor providing an electrical response linear with respect to oxygen concentration. The electrical response is converted into a signal proportional to the time rate of change of oxygen and this signal is recorded and the maximum recorded signal determines the quantity of glucose initially present.

In enzyme assay, equal samples of buffered enzymes are added to an excess of substrate in the presence of a concentration sensor. The electrical response is again converted directly to a time rate of change signal and this signal recorded. The maximum rate recorded is proportional to enzyme activity.

One of the problems inherent in the direct differentiation system of this invention is that any noise produced by the sensor is amplified by the derivative response. This problem is also aggravated by constant stirring of the liquid in which the electrode is submerged. These problems are met by an improved polarographic oxygen electrode constructed in accordance with the present invention in which the membrane is stretched very tightly over the cathode surface.

A more thorough understanding of the invention may be obtained by a study of the following detailed description taken in connection with the accompanying drawings, in which.

DESCRIPTION OF THE PREFERRED EMBODIMENTS

The Rate Sensing System

Figure 1:
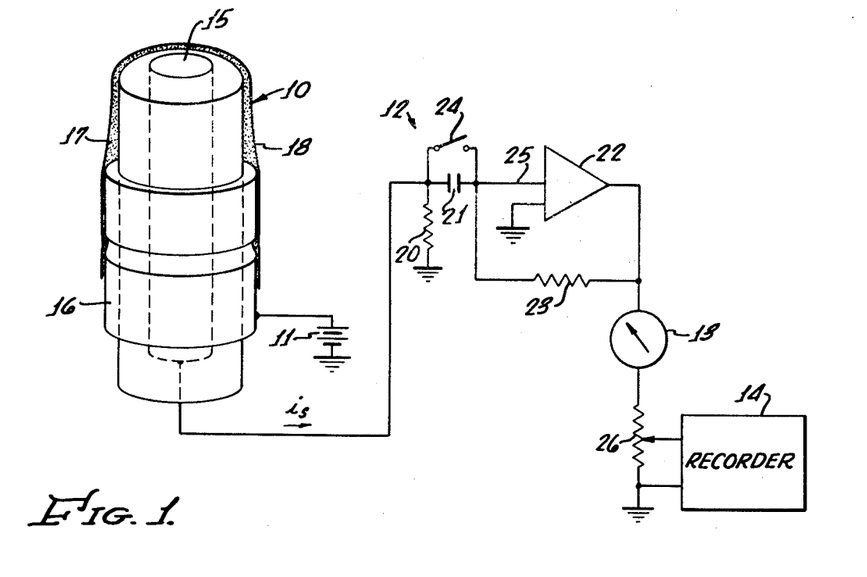
FIG. 1 is a block diagram of a direct rate sensing analyzer system.

A simplified block diagram of the rate sensing system of this invention is illustrated in FIG. 1, the system comprising a sensor 10, a voltage source 11, an electrical differentiating means 12 and either a meter 13 or recorder 14 or both as shown. In the embodiment shown, sensor 10 comprises a polarographic oxygen sensor. This type of electrode is presently manufactured and sold by Beckman Instruments, Inc. utilizing the teachings of U.S. Pat. No. 2,913,386 — Clark, Jr. as the Beckman Oxygen Sensor. This electrode includes an interior gold cathode electrode 15 and an annular outer silver anode electrode 16. An electrolyte forming substance 17 is retained in electrical current contact with the anode and cathode by a permeable membrane 18 electrically insulating the electrolyte. The anode is connected to the voltage source 11 which is typically 0.8 volts. The sensor output signal — the cathode current $i_S$ — is directly proportional to the oxygen concentration in a reagent solution in which the electrode is submerged, i.e., $$i_s = Kc \qquad (1)$$

where c is the concentration of oxygen. This current is connected to the input of the differentiating means 12.

Differentiation circuit 12 provides a means for directly differentiating the current $i_S$ produced by the sensor 10 to provide an output which is proportional to the time rate of change of oxygen concentration. As shown this circuit includes a resistor 20 connected between the cathode and ground, a capacitor 21 connected between the cathode and the input of an operational amplifier stage 22 including feedback resistor 23, and a shunting switch 24 connected across the terminals of the capacitor. Resistor 20 converts the sensor current to a voltage. The rate of change of this voltage is then converted into a current i by capacitor 21 which is applied to the amplifier input terminal 25. This current is defined by the equation $$i = RC \frac{di_S}{dt} \qquad (2)$$

where R is the resistance of resistor 20, C is the value of capacitor 21 and $i_S$ is the sensor current. The output voltage $V_o$ of the operational amplifier is then defined by the product of this current and its feedback resistance, i.e., $$V_o = i \cdot R_f = R_f RC \frac{di_S}{dt} \qquad (3)$$

where $R_f$ is the resistance of feedback resistor 23. Combining equations 1 and 3, $$V_o = KR_f RC \frac{dc}{dt} \qquad (4)$$

or $$V_o = K' \frac{dc}{dt}, \text{ i.e.} \qquad (5)$$

the output voltage $V_o$ is proportional to the time rate of change of oxygen concentration.

Output voltage $V_o$ is read on the voltmeter comprising micro-ammeter 13 and series potentiometer resistance 26 or recorded on recorder 14 which is connected between ground and the movable contact of the potentiometer 26.

Shunting switch 24 provides a means for directly connecting the sensor current to the amplifier. In this mode of operation, the capacitor 21 is shunted and the resistor 20 is also effectively shunted since the negative feedback of the amplifier maintains its input terminal 25 at ground potential. The system then functions as a direct oxygen concentration measuring system.

Figure 2:
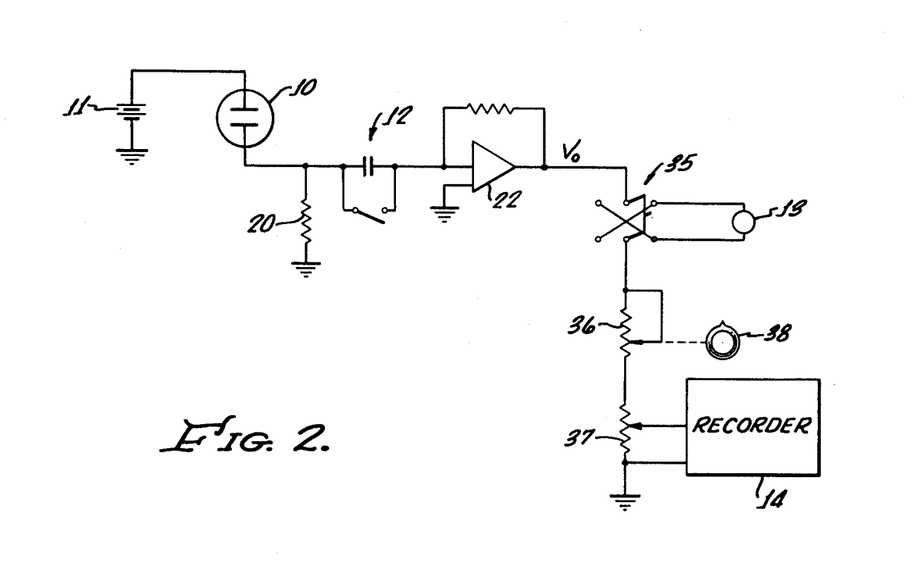
FIG. 2 is a more detailed circuit schematic of the rate sensing system.

A more detailed circuit schematic of the rate sensing system is shown in FIG. 2. The sensor 10, voltage source 11 and electrical differentiating means 12 are connected as shown in FIG. 1 and described above. The output voltage $V_o$ at the output of the operational amplifier 22 is connected to a double pole-double throw reversing switch 35 which selectively reverses the polarity of the micro-ammeter 13. The series resistance connecting this meter to ground includes a variable resistance 36 and a potentiometer 37.

Changes in oxygen level of a reaction may be in either a positive or negative direction; hence, the derivative output may be a positive or negative going signal. The reversing switch 35 therefore permits the direction of the meter reading to be reversed in accordance with the reaction being monitored.

The variable resistor 36 permits the signal level delivered to the meter and recorder to be varied for a given output signal. Advantageously, resistor 36 is a multi-turn device with its control arm coupled to an indicating dial 38 such as the turns counting dial sold by Beckman Instruments, Inc., assignee of the present invention under the trademark "Duodial." As one example of the utility of the variable resistance 36 and turns counting dial 38, if a standard sample is run with the dial set at 1,000 and a 78 percent response is measured on the meter 13 or recorder 14, this standard can be made to give a full-scale response on the meter and recorder by resetting the turns counting dial to 780.

The upper and lower limits of electrical (RC) time constant of the differentiating portion of the circuitry are determined primarily by two factors: On one hand, it is desirable to use as high an RC product as possible since this product is the multiplier which scales the amplifier current as a function of the rate of change of sensor current. On the other hand, the time constant must be sufficiently short so that the capacitor will reach its peak voltage at substantially the time of the maximum rate of the reaction being monitored. For example, when the rate sensing system is used for monitoring a reaction in which the peak response is reached 20 seconds after sample introduction, the RC time constant should be 4 seconds or less in order to insure that the capacitor is 98 percent charged at the time of peak response.

In the circuits of FIGS. 1 and 2, the resistance value of resistor 20 must be sufficiently low so that the sensor voltage is not substantially reduced below its normal operating level of 0.8 volt. A representative sensor current for an air saturated solution is about $1.7 \times 10^{-6}$ amps; it is therefore desirable that this resistor have a value of less than 60 K ohms in order to prevent the voltage drop across resistor 20 from exceeding 0.1 volt. The upper limit on the value of the capacitor 21 is then 67 $\mu$fd for a 60 K ohm resistor 20 and a time constant of 4 seconds.

Reactions which liberate oxygen may provide sensor currents higher than those for the example given of an air-saturated solution, e.g. the catalase reaction in which oxygen is liberated. A shorter time constant is then advantageously used, employing for example a 25 K ohm resistor and a 100 $\mu$fd capacitor with a resulting RC time constant of 2.5 seconds.

Figure 3:
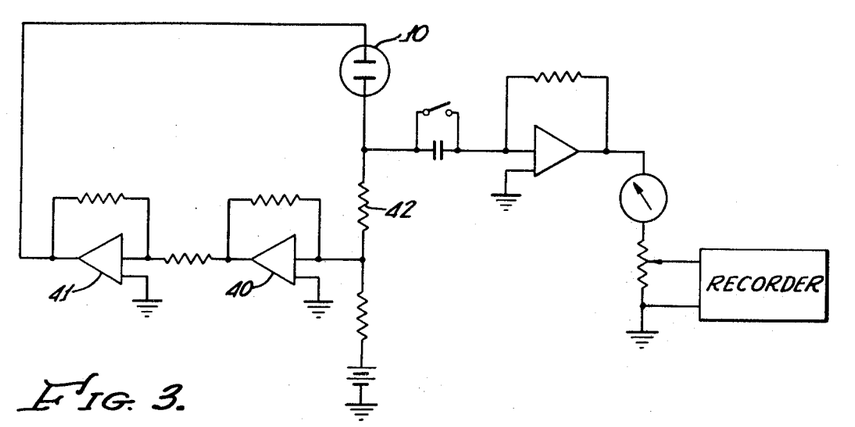
FIG. 3 is a schematic of the rate sensing system in which additional amplifier stages maintain a constant voltage across the sensor.

Substantially higher values of resistance in the differentiating circuit can be employed in the circuit of FIG. 3. In this embodiment, a first operational amplifier 40 serving as a summing amplifier and a second operational amplifier 41 serving as an inverting amplifier maintain a nearly constant voltage across the sensor regardless of the value of current drawn therefrom. In this embodiment, the resistance value of resistor 42 may be of the order of 500 K ohms so that the capacitor value can be lowered to the order of 5 $\mu$fd for a 2.5 second time constant. This lower value of capacitance is particularly advantageous since it may be provided by a good quality, non-electrolytic capacitor. The electrolytics, normally required for the higher values of capacitance such as 67 $\mu$fd, may have a significant leakage current and tend to be noisy.

The meter and recording portions of the system of FIG. 3 may be the same as described above and shown in FIGS. 1 and 2.

Figure 4:
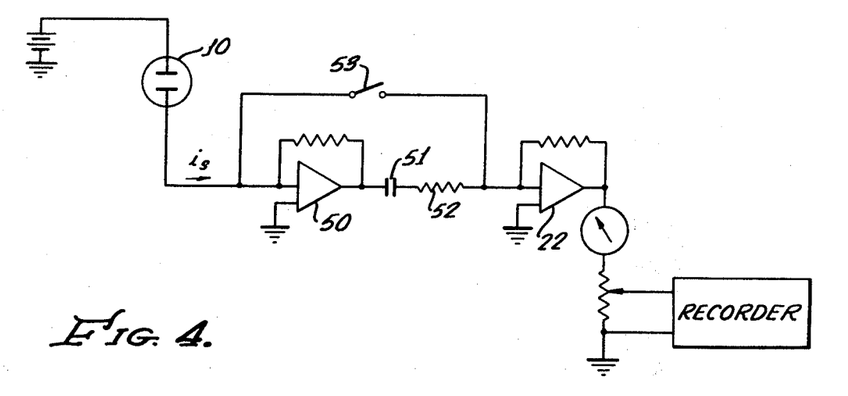
FIG. 4 is a schematic of another embodiment of the rate sensing system utilizing a dc preamplifier between the sensor and the differentiating circuit.

Another embodiment of the rate sensing circuitry is shown in FIG. 4 including a direct current operational amplifier 50 used as a preamplifier for the output signal of the sensor 10. The output of this preamplifier is connected to a series circuit comprising the differentiating capacitor 51 and a resistor 52, this circuit being connected to the input of the operational amplifier 22. Resistor 52 and capacitor 51 provide a predetermined time constant, e.g. a resistance value of 1 megohm and a capacitance value of 2 $\mu$fd give a 2 second time constant. The meter and recorder are connected to the output of the amplifier 22 in the manner described above. Switch 53 permits the preamplifier and differentiating capacitor to be bypassed to provide the operational mode in which the oxygen is directly recorded.

The preamplifier 50 operates to maintain fixed voltage across sensor 10, regardless of the value of the sensor current $i_S$. In addition, the preamplifier provides a voltage level at its output which is substantially higher than the allowed voltage at the sensor cathode; therefore, the RC time constant can be reduced and a non-electrolytic capacitor of the order of 2 $\mu$fd used for the differentiating capacitor 51 — such capacitors being obtainable at high quality and relatively low cost.

THE POLAROGRAPHIC OXYGEN SENSOR

Figure 5:
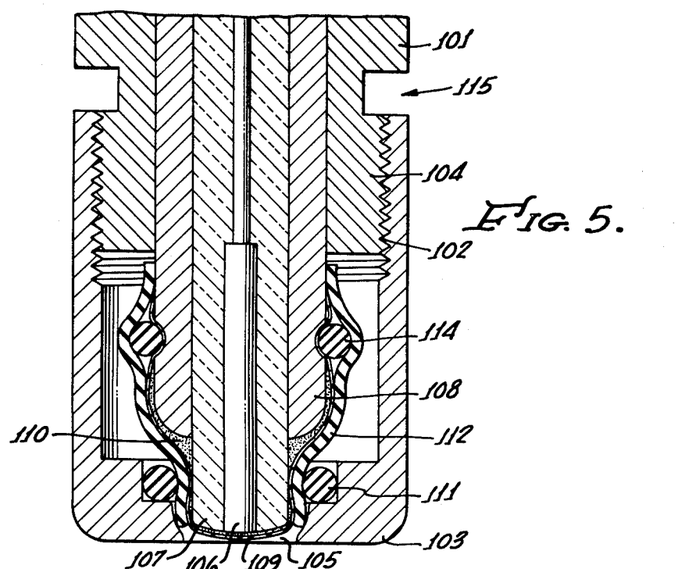
FIG. 5 is a cross-sectional view of the cap and cathode end of the modified polarographic sensor.

Any noise produced by the sensor 10 is especially undesirable because of the noise-amplifying characteristics of the differentiation circuitry. This problem is further aggravated when, as described hereinafter, the electrode is utilized in a stirred liquid system in which there are varying liquid forces placed upon the membrane. FIG. 5 illustrates a sensor constructed in accordance with this invention which is characterized by a very low noise output and high stability over long time periods. This figure illustrates in detail the cap and membrane portion of the sensor. Reference is made of U.S. Pat. No. 2,913,386 — Clark, Jr., for a detailed structure and functional description of the polarographic sensor.

As shown in FIG. 5, the body 101 of the sensor terminates in an externally threaded member 102 from which extends the sensor element comprised of a central cylindrical gold cathode 106 surrounded on its side successively by an epoxy member 107 and an outer silver anode 108. A one mil tetrafluoroethylene membrane 109 such as Teflon fits over the anode and cathode and retains the KCl gel electrolytic substance 110 in electrical current carrying contact between the two electrodes. An outer elastomeric sleeve 112 made from a material such as silicone rubber tubing holds the membrane snugly against the sides of the cathode and draws the membrane more tightly against the outer face of the cathode.

A hollow cylindrical cap 103 provided with internal threads 104 is screwed down over the sensor element exposing the face of the cathode and membrane through the opening 105. A small O-ring 111 depending on dimensions of the head of the sensor may be provided in cap 103.

The cap 103 is thoroughly tightened onto the base 101, stretching the membrane 109 very tightly over the cathode surface. Improved signal to noise ratios are obtained when the membrane is stretched and stressed to the point where the membrane just begins to show the whitening chracteristic of crystallization. Heretofore, this condition has been deliberately avoided since it was considered that the membrane was then stretched too tightly for satisfactory functioning of the electrode. The membrane should not, however, be stretched beyond this point since additional stretching will cause the membrane to become insufficiently permeable for satisfactory use. A preferred method of assembly is to connect the sensor in the rate sensing system, as described above and illustrated in FIGS. 1–4, and observe the sensor noise level on the recorder 14 in air and in stirred water as the cap 103 is tightened onto the base 101. The tightening is continued until the noise level is reduced to a predetermined level. The sleeve 112 of silicone rubber tubing over the membrane at the cathode end of the sensor holds the membrane snugly against the sides of the cathode end of the sensor as well as aiding in drawing the membrane more tightly against the face of the cathode. During assembly of the sensor, the membrane 109 is first put on in its normal fashion, retained by its usual outer O-ring 114. The outside of the membrane is then lubricated with water or with electrolyte gel and the silicone rubber sleeve 112 is pushed gently over the end of the sensor. The small O-ring 111 in the cap may be eliminated depending on the dimensions of the sensor. The silicone rubber sleeve also greatly reduces evaporation of water from the sensor electrolyte.

Sensors constructed in the manner described are characterized by high sensitivity and low noise. Further, these sensors are quite insensitive to the solution vibration that is associated with stirring, while providing an efficient contact between the sensor and the liquid in a small volume reaction chamber. Also, the sensor response is highly stable over the period of its use. Thus, response sensitivity in day-to-day operation, using the same sensor, is well within the range to be expected from the effect of the temperature variation alone.

AUTOMATED BATCH ANALYZER

Figure 6:
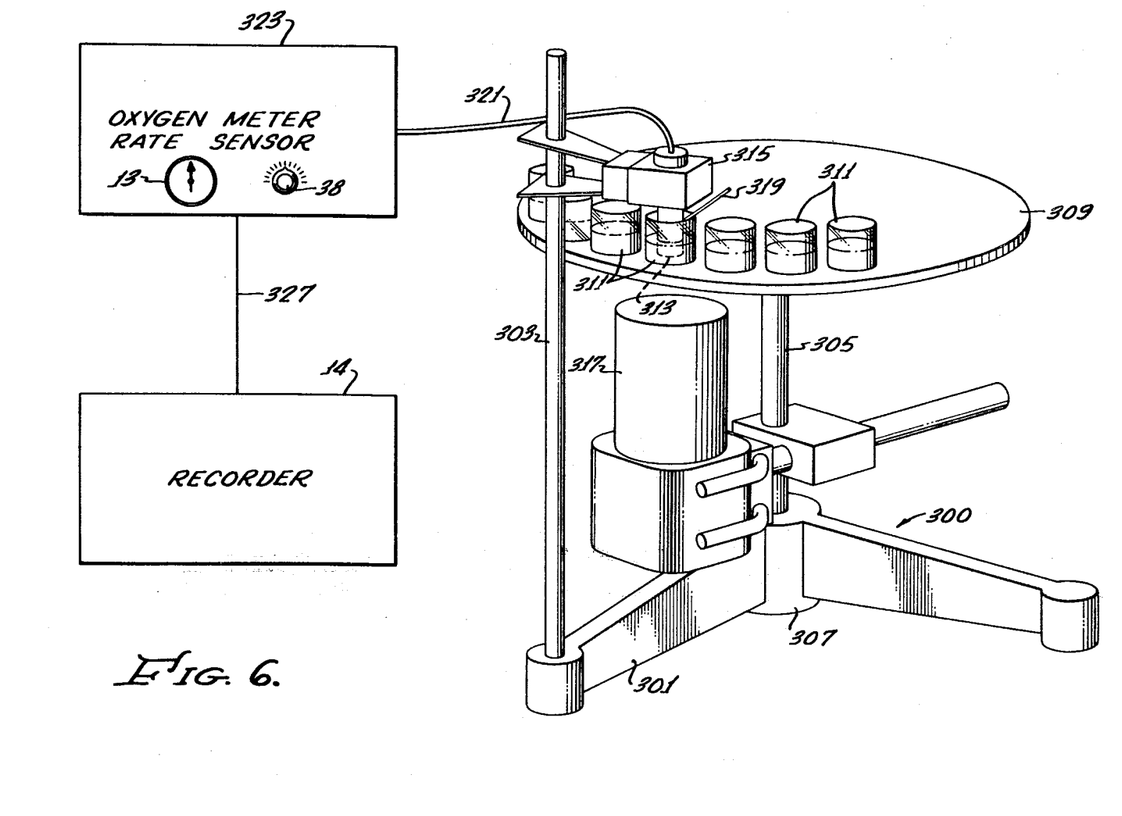
FIG. 6 is an embodiment of a partially automated batch oxygen analyzer constructed according to the invention.

With reference to FIG. 6, an embodiment of a portable, automated system for the invention includes a stand 300 with a base 301 supporting a first vertical support rod 303 and a second shorter rod 305. The second rod 305 is mounted in a bearing socket 307 and the rod carries a horizontal turntable 309 mounted to rotate around the axis of the rod 305. A series of sample cups 311 are carried near the outer circumference of the turntable and each cup successively passes under the polarographic sensor electrode 313 which is connected to an electrode clamp 315 slidably mounted on the longer rod 303. Immediately beneath the electrode 313 is disposed a constant speed magnetic stirrer 317. Each sample cup contains a magnetic stirrer bar, not shown.

The sensor electrode 313 is connected by conductors 321 to rate sensing oxygen meter 323 including direct differentiation means as described above and having a readout meter 13 and turns counter dial 38 associated with the voltmeter and a conductor 327 connected to an ink pen recorder 14.

In substrate determinations, an equal amount of buffered enzyme is placed in each sample cup 311. The turntable 309 is rotated so that the first sample cup 311 containing a stirrer bar is placed over the stirring motor 317 and the sensor electrode 313 is lowered onto the same position in each cup. After equilibration into the sensor, a calibration amount of a substrate is added by means of a micropipette 319 to the sample cup and the meter and recorder are calibrated to read 0–100 percent full scale for a series of determinations. The remaining sample cups are then run successively by rotating into assay position and adding a set amount of substrate sample from the pipette 319 and the maximum rate is read either from the readout dial 325 of the meter 323 or from the maximum peak of the recorder 14.

An alternative procedure is to utilize a single enzyme sample and to successively add substrate samples to the single enzyme sample. This procedure entails a downwardly drifting maximum line and requires more numerous calibrations but utilizes less enzyme.

The procedure discussed above is reversed in enzyme activity determinations, the sample cups containing the substrate and unknown activity enzyme samples are added to the known quantity of substrate.

Although of general application to chemical reactions and particularly to enzymatic reactions, specific very important applications relate to the assay of batch or static reactions using oxygen as a co-substrate in direct reaction with oxidases, oxygenases or hydrolases, or enzyme reactions in which oxygen is liberated. Representative enzymes of interest are listed below.

TABLE I

Glucose oxidase
Cholesterol oxidase
Galactose oxidase
Xanthine oxidase
Pyruvate oxidase
Pyridoxaminephosphate oxidase
Diamine oxidase (histaminase)
Urate oxidase
Ascorbate oxidase
Phenylalanine-4-hydroxylase
Homogentisate oxidase
Meso-inositol oxygenase
Tryptophan oxygenase
Lipoxidase
Kynurenate hydroxylase
Dopamine hydroxylase
Polyphenol oxidase (tyrosinase)
Moncamine oxidase
Steroid hydroxylases
Cytochome oxidase
Snake venom-L-amino acid oxidase
Catalase

BATCH ANALYZER MONITORING OF TISSUE AND BODY FLUID CATALASE

In one of its aspects, the present invention provides a new and convenient method for monitoring tissue and body fluid catalase which is present in most epithelial cells including both red and white cells. Interest in catalase is rapidly increasing since there are some suggested links between catalase activity and cancer, a recent study showing an immunological relationship between C-reactive protein and catalase and in the disease acatalosemia, red cells exhibit a deficiency in catalase. Because of the high rate constants of the reaction of catalase with hydrogen peroxide, catalase assay provides an extremely sensitive monitor for many clinical conditions such as hemolytic conditions during transfusions and, with the sensitivity of the present method, vascular accidents of the central nervous system such as brain hemorrhaging and diseased states of the nervous system, can be detected through catalase assay of cerebrospinal fluid since catalase activity is not found in the normal state.

In the prior art spectrophotcmetric an titrimetric methods, the human tissue itself particularly interferes with monitoring the presence of catalase therein. Manometric methods can be used for continuous monitoring but are slow and give low values on an absolute basis. Enzyme assay cannot be performed using a stoichiometric method since enzyme activity affects only the rate, not the stoichiometry.

Figure 7:
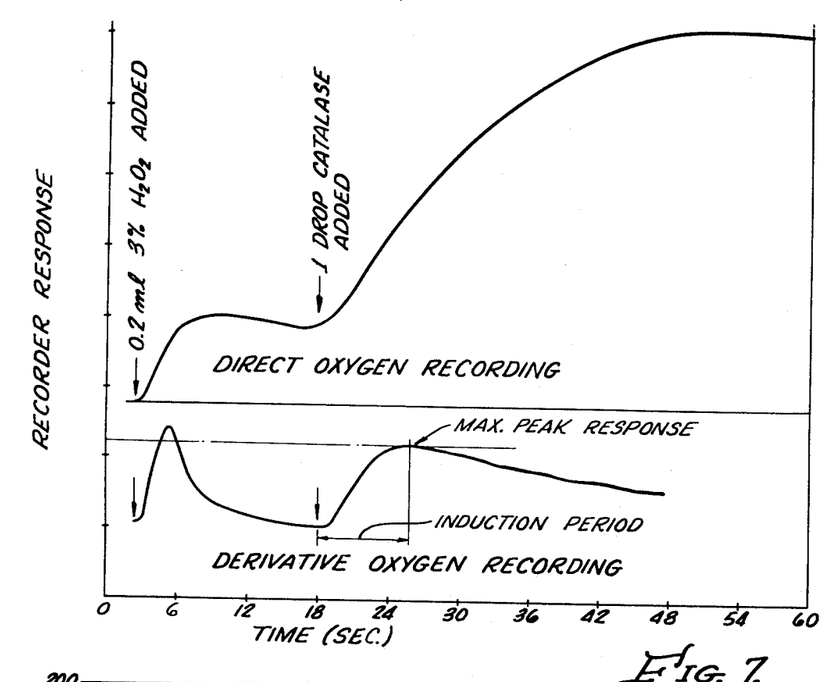
FIG. 7 is a graphical comparison of direct to derivative recording for the catalase-$H_2O_2$ system.

In the method of the invention, the polarographic oxygen sensor provides a quick and extremely sensitive measure of catalase activity through monitoring the increase in dissolved oxygen concentration with time of reaction. With a potential of 0.8 volts applied to the anode, current is obtained only when oxygen is reduced at the cathode establishing a current signal proportional to the rate of diffusion of oxygen through the membrane and hence to the partial pressure of oxygen in the medium. As the catalase induced decomposition of hydrogen peroxide proceeds, oxygen is liberated and the direct mode of thee oxygen meter current increases as shown in the upper curve of FIG. 7. The rate sensing meter of the invention directly furnishes a first derivative or rate sensing response in the form of a signal proportional to the rate of change of oxygen concentration as shown in the lower curve of FIG. 7.

Figure 8:
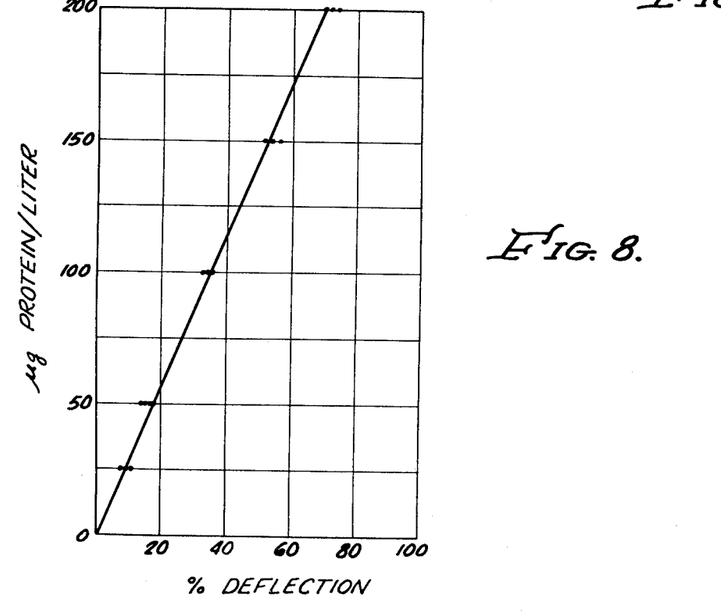
FIG. 8 is a graph illustrating the linearity of maximum rate response versus concentration.

To measure catalase activity, the slope of the oxygen concentration-time curve must be determined at a given peroxide concentration. Looking again at the derivative curve, there is an apparent induction period corresponding to the mixing time as the rate rises to a maximum peak response in less than 30 seconds after sample introduction and then declines due to oxygen super-saturation of the solution and to decreasing substrate concentration. The actual initial rate can be found from the derivative response curve by extrapolation. The peak response has been found to be directly proportional to the product of enzyme and substrate concentrations over more than a hundred-fold range. The results of a linearity enzyme run are shown in FIG. 8. Therefore, use of a fixed substrate concentration provides a linear enzyme assay. Since linearity is also found with the peak response which corresponds to the apparent maximum or maximum observed rate, the unnecessary extrapolations, calculations and slope determinations can be avoided and the data is obtained instantly and directly.

EXAMPLE 1 — CATALASE ASSAY

A series of tissue homogenate samples were assayed utilizing the apparatus of FIG. 6. An excess of buffered peroxide solution (10 ml) from a few tenths to a hundredth molar were placed in 30 ml beakers, though it has been shown that as little as 1 ml of solution can be monitored in a 5 ml cup. The magnetic stirrer is turned on and the sensor is inserted into the identical position in each cup to remove influence of mixing on the results.

Calibration data were obtained on a stock solution containing 20 mg/ml of bovine liver catalase preparation. This material was run at dilutions ranging from 1:1,000 to 1:100,000. Normally, runs were made by adding 100 or 200 microliters of enzyme to 10 ml of 0.0067 M $H_2O_2$ in a 0.025 M phosphate buffer at pH 6.86. Data were also obtained at higher peroxide levels, particularly for weaker enzyme preparations. In the latter case, peroxide up to 0.4 M was used and buffer strength was as high as 0.1M. In the studies of tissue homogenates, 1 ml of 10 percent tissue homogenates were added to 30 ml of 0.4 M hydrogen peroxide in pH 6.86 phosphate buffer. The data obtained from runs on human tissue homogenate samples from two different human subjects are reported in the following table.

Table II

| Catalase Activities in Various Human Tissues Bovine Catalase Units in 1 ml of 10% Tissue Homogenate | | |
|---|---|---|
| Tissue | N (age 2) | M (age 4–½) |
| Liver | 431 | 1770 |
|  |  | 1590 |
| Kidney | 100 | 367 |
|  |  | 434 |
| Lung | 139 | 78 |
|  | 84 |  |
| Intestine | 96 | — |
| Spleen | 93 | — |
| Adrenal | 70 | — |
| Heart | 57 | 79 |
| Skeletal Muscle | 30 | — |
| Pancreas | 30 | 64.5 |
| Testis | 21 | — |
| Cerebrum | — | 12 |
| Cerebellum | — | 6 |

Survey runs were also made on a series of cerebrospinal fluid samples. Most of the samples were clear and gave no catalase response.

A very few samples were xanthochromic (yellow) indicating presence of catalase containing red blood cells in the fluid. The samples came from a patient where brain hemorrhaging was known to have occurred and each sample registered a catalase response. One sample was absent yellow coloration but produced a significant catalase response. The catalase response was verified by a repeat run to which the catalase inhibitor sodium azide was added and the absence of catalase response showed that the previously observed response was due to catalase activity. Thus, catalase assay of spinal fluid with the rate sensing analyzer of the invention is far more sensitive than the previously practiced visual observation of spinal fluid samples.

A comparison of the rate sensing batch analyzer of the invention with the titanium-complex spectrophotometric method on bovine liver catalase samples showed the spectrophotometric method to be of relatively low sensitivity requiring enzyme concentrations of at least 80 micrograms per liter whereas good results could readily be obtained with 50-fold lower concentrations with the batch analyzer.

DETERMINATION OF GLUCOSE LEVEL IN BLOOD AND URINE

For the clinical determination of glucose in blood and urine, it is necessary to have rapid procedures and instrumentation that enable the quick and reliable determination of true glucose content. The instrument should be manual and portable and be capable of handling the total requirements of the analysis of all the daily samples from a hospital or laboratory. The analysis of blood and urine glucose is a major procedure in the clinical laboratory, a typical 250 bed hospital requiring 18 to 25 determinations daily. The number of determinations is limited by convenience and more samples would be run if they could be analyzed quickly and inexpensively.

With reference to analysis of batch enzyme samples, and particularly to the determination of glucose by enzymatic methods, the method most widely employed in the United States utilizes the Folin-Wu reagent on a blood sample from which proteins have been removed by precipitation with tungstic acid. This method is a totally reducing procedure relying on measurement of color. The method suffers from poor accuracy; the results obtained are 10–20 mg percent higher than absolute glucose content, which is to be expected with a non-specific method, and color fading is another serious obstacle to this procedure. The Folin-Wu method takes about one hour to set up each day and has the additional disadvantage that it does not measure true glucose but responds to all reducing substances. If a person, for example, had galactosemia, his glucose level would appear abnormally high. Protein precipitation and filtration steps are necessary for one employing this method.

An ideal instrument would be set up rapidly, make the determinations rapidly, using a small sample size and would measure true glucose. The small sample size is particularly important in pediatric determinations and rapid set-up time is important in stat, that is immediately required off-hours, analyses. These criteria are fulfilled by the methods and apparatus of this invention.

Because of the general importance of blood glucose determination for diagnostic purposes, this measurement has been the subject of numerous investigations which have led to the development of a plethora of methods. The methods are reviewed by Richard J.

Henry's "Clinical Chemistry, Principal and Technics," Harper % Rowe, New York, (1965). They can be broadly classified into reducing methods, color forming methods, and enzymatic methods based on either glucose oxidase or hexokinase plus glucose-6-phosphate dehydrogenase.

The glucose oxidase reaction is invariably specific to presence of glucose and in the assay procedure of the invention does not require the time consuming and difficult preliminary precipitation of proteins, nor is it dependent on other factors or impurities which have heretofore been believed to affect the glucose oxidase method. Glucose oxidase catalyzes the oxidation of glucose by molecular oxygen to gluconic acid and hydrogen peroxide. This reaction is highly specific to $\beta$-D-glucose. It has been adapted to many forms of measurement such as oxygen uptake, peroxide formation and gluconic acid formation. There are several other methods based upon the measurement of hydrogen peroxide or of some product of its reaction with other agents such as various chromogens and these methods are all subject to uncertainty due to the highly reactive nature of peroxide with other reducing substances present in the sample or the peroxide may be decomposed by impurities in the enzyme such as catalase. Because of this, measurement of oxygen decrement or gluconic acid formation probably furnish the most nearly ideal means of true glucose measurement.

In one of the prior automated batch methods, hydrogen peroxide is reacted with the chromogenic hydrogen donor, o-dianisidine, which reacts in the presence of peroxidase to form a colored substance that is stoichiometrically related to the concentration of glucose. The color change is followed by spectrophotometric recording. The incubation time, however, is 5 to 15 minutes for the primary action plus 10 to 15 minutes for color development. The presence of peroxidase inhibitors or peroxide reducers often interferes with the chromogen reaction. A negative error is produced by ascorbic acid levels greater that 5 mg/100 ml. Bilirubrin and hemolysis also interfere and each one mg of uric acid per 100 ml causes a decrease in the color approximately equivalent to 1 mg glucose per 100 ml. Therefore, for urine samples, it is necessary to remove interfering substances with an ion exchange resin before a determination can be run. These substances do not interfere with the oxygen-based glucose-oxidase method. Apparently, all of the commonly cited interferences with the glucose oxidase method are, in fact, interferences with the peroxide-peroxidasechromogen system. This is most strikingly demonstrated by the applicability of the present method to untreated urine samples.

Stirring is generally necessary in the glucose assay of the invention because the presently available oxygen sensors are subject to concentration polarization. Best results are obtained with a synchronous motor driven stirrer providing a selected constant stirring speed of between 5–10 revolutions per second (rps) with a 3 ml sample size. At speeds greater than 12 rps, the vortex created by stirring tends to draw bubbles down to the sensor tip. Responses to samples containing ⅛ inch D × ½ inch long stirring magnet bars are virtually unaffected by stirring as long as a steady speed is maintained.

The proportionality of the glucose monitor is dependent on the reaction rate being free of influence of oxygen. The oxygen requirement is affected by sample volume, enzyme activity, oxygen solubility and the oxygen contributed by peroxide decomposition.

Since the rate of reaction is proportional to the substrate (glucose) concentration, the maximum rate for a given glucose sample size will be higher with smaller total volumes of solution; hence, the same rate will be obtainable at a lower enzyme concentration and cost if a smaller solution volume is used. A possible limitation on minimum solution volume is the amount of oxygen required. The solubility of oxygen in water at 22°C. is about $2.76 \times 10^{-4}$ M, so that 1 ml of air-saturated water contains about $2.76 \times 10^{-7}$ moles of oxygen. A sample of 100 $\mu$l containing 200 mg percent glucose, the highest amount usually present in blood, will have $1.12 \times 10^{-6}$ moles of glucose, of which 63 percent or $7 \times 10^{-7}$ moles is in the $\beta$-form and thus will react with an equal number of moles of oxygen in the presence of glucose oxidase (provided that the hydrogen peroxide is destroyed in a path not leading to oxygen release). Hence, 3 ml of air-saturated water appears necessary for complete reaction of the available maximum glucose in 100 $\mu$l of 200 mg percent solution. Since the maximum rate is reached when less than half of the glucose has reacted, the oxygen in 3 ml of air-saturated water gives valid rate data for 100 $\mu$l samples of 300–400 mg percent glucose. In a 2 percent NaCl solution at 30°C. the oxygen solubility is only $1.91 \times 10^{-4}$ M. Thus, if the oxygen solubility is appreciably lessened by salting out effects or elevated temperature, or if the solution is appreciably below saturation due to oxygen depletion by impurities within the enzyme solution, the volume of enzyme solution should be larger than 3 ml in these cases.

Impurities present in glucose oxidase enzyme cause continuous depletion of oxygen on standing and unless controlled, are a cause of erratic performace of the monitor. The depletion can be due to bacterial action or internal hydrolytic reactions.

Impure glucose oxidase preparations contain carbohydrases which hydrolize larger carbohydrate impurities splitting off glucose as a product. If either the carbohydrates or carbohydrases are lacking, there is no glucose formed and the oxygen level is stable. DEAE cellulose purification can be utilized to remove these impurities. The hydrolytically produced glucose, of course, reacts with the oxygen in the presence of glucose oxidase to deplete the oxygen level in the enzyme solution. Even with aeration by bubbling, shaking, or stirring, the oxygen level of the impure enzyme solution continues to decrease until finally the level becomes so low that all of the remaining oxygen is consumed by the introduction of even small samples of glucose. The apparent maximum rate reached under these conditions is highly irreproducible.

Bacteria are not well controlled by quaternary amines. However, the presence of iodine and molybdate catalyst has been found to both inhibit bacterial growth indefinitely and to simultaneously permit peroxide decomposition without oxygen liberation. Most enzyme preparations contain sufficient amounts of catalase to decompose appreciable amounts of hydrogen peroxide. This undesired influence on the oxygen stoichiometry is further controlled by the addition of 5% ethanol which is believed in the presence of catalase to be oxidized by peroxide to acetaldehyde without liberation of oxygen.

For direct rate-sensing methods employing direct differentiation for the conversion of the sensed signal into a signal proportional to the time rate of change of oxygen concentration to give reaction rate signals readily distinguishable from system noise, it is important that the reaction be made to go to completion in a short time. Choice of enzyme activity to provide for 75 to 98 percent completion of the enzymatic reaction in one minute has been found suitable. This requires that the reaction have a time constant, determined by the enzyme activity employed, of approximately 15 seconds. The enzyme activity is determined from the rate expressions, $$\text{Rate} = -\frac{d(G)}{dt} = K \cdot (E)(G) \quad (6)$$

where G is glucose concentration and E is enzyme units;

$$-\frac{dG}{dt} = kE \cdot G, \text{ and} \quad (7)$$

$$\ln \frac{Go}{G} = k E t, \quad (8)$$

where Go = glucose at initial air saturated solution conditions, t = τ, the time constant, when Go/G = e, the base of natural logarithms. Thus, $$\tau = 1/kE = 1/\left(-\frac{dG/G}{dt}\right) \quad (9)$$

For E units of enzyme in 3 ml of solution, with each unit decomposing 1 μmole glucose/min.

$$\frac{E \text{ units}}{3 \text{ ml}} = \frac{10^{-6} \text{ moles glucose/min.}}{3 \text{ ml}} \cdot E = -\frac{dG}{dt} \quad (10)$$

Since the unit is defined for 3 percent glucose $$\left(=\frac{3 \text{ gms.}}{100 \text{ cc}} = \frac{30 \text{ gms.}}{\text{liter}} \times \frac{1 \text{ mole}}{180 \text{ gms.}} = \frac{1}{6} \frac{\text{mole}}{\text{liter}}\right),$$

$$-\frac{dG/G}{dt} = \frac{10^{-6}}{3} \times 6 \frac{\text{liters}}{\text{ml. min.}} \times \frac{1000 \text{ ml.}}{\text{liter}} \cdot E = 2E \times P \, 10^{-3} \text{ min.}^{-1}$$

and = KE for a 3 ml. sample. Hence, k = 2 × 10⁻³ min.⁻¹. For a time constant of ¼ min., $$\tau = \frac{1}{4} \text{ min.} = \frac{1}{kE} = \frac{1}{E \cdot 2 \times 10^{-3} \text{ min.}^{-1}}$$

$$E = \frac{4}{2 \times 10^{-3}} = 2000 \text{ units in 3 ml.}$$

The required enzyme concentration of about 666 units/ml for a time constant of 15 seconds will be applicable regardless of the volume of solution employed. In practice enzyme of 500 units/ml activity is normally employed although as little as 200 units/ml or as much as 750 units/ml can be employed successfully. With sensor noise a few percent of maximum signal level and enzyme of this activity, the maximum rate can be obtained essentially within mixing time and then fall off rapidly furnishing a clear peak response in a short time, repeatable accurately, on multiple samples.

Glucose oxidase systems exhibit useful activity in the pH range of about 4.5 to 8.0 dropping off sharply on either side. The optimum pH is 5.6 to 6.0 As long as the aqueous phase is kept saturated with oxygen, the rate of reaction is virtually unchanged from 15°C. to 60°C. However, large errors are introduced into the assay if temperature is not maintained constant. Responses measured at 21.5°C. and 30°C varied from 46.9 percent to 60 percent corresponding to a mean temperature change of 5.4 percent per degree. This is due to the temperature coefficient of the sensor, to the decreased oxygen solubility with increasing temperature and to the increased rate of reaction at higher temperature.

Frequent interspersing of calibration standards between each 5 to 10 runs or every 15 to 30 minutes successfully compensates for temperature changes but calibration can be reduced by the use of a thermostated reaction vessel, preincubation of the reagents and vessel or by electronic compensation for the temperature effect by means of a thermistor.

Although the batch glucose monitor response is not perfectly linear, it is so nearly linear that corrections generally need not be made. With standardization at the 100 percent glucose level, responses are within 1 – 2 percent of directly proportional to glucose concentration up to greater than 150 mg percent and within 2 – 5 percent of linear at 200 mg percent — thus, "normal" glucose levels are accurately evaluated, and only slight inaccuracy results even when abnormally high glucose levels are calculated from a 100 mg percent standard. If accuracy is required for a high glucose sample, a standard containing 200 mg percent or 300 mg percent glucose can be employed or the sample can be suitably diluted to bring it into the 100 mg percent range.

Figure 9:
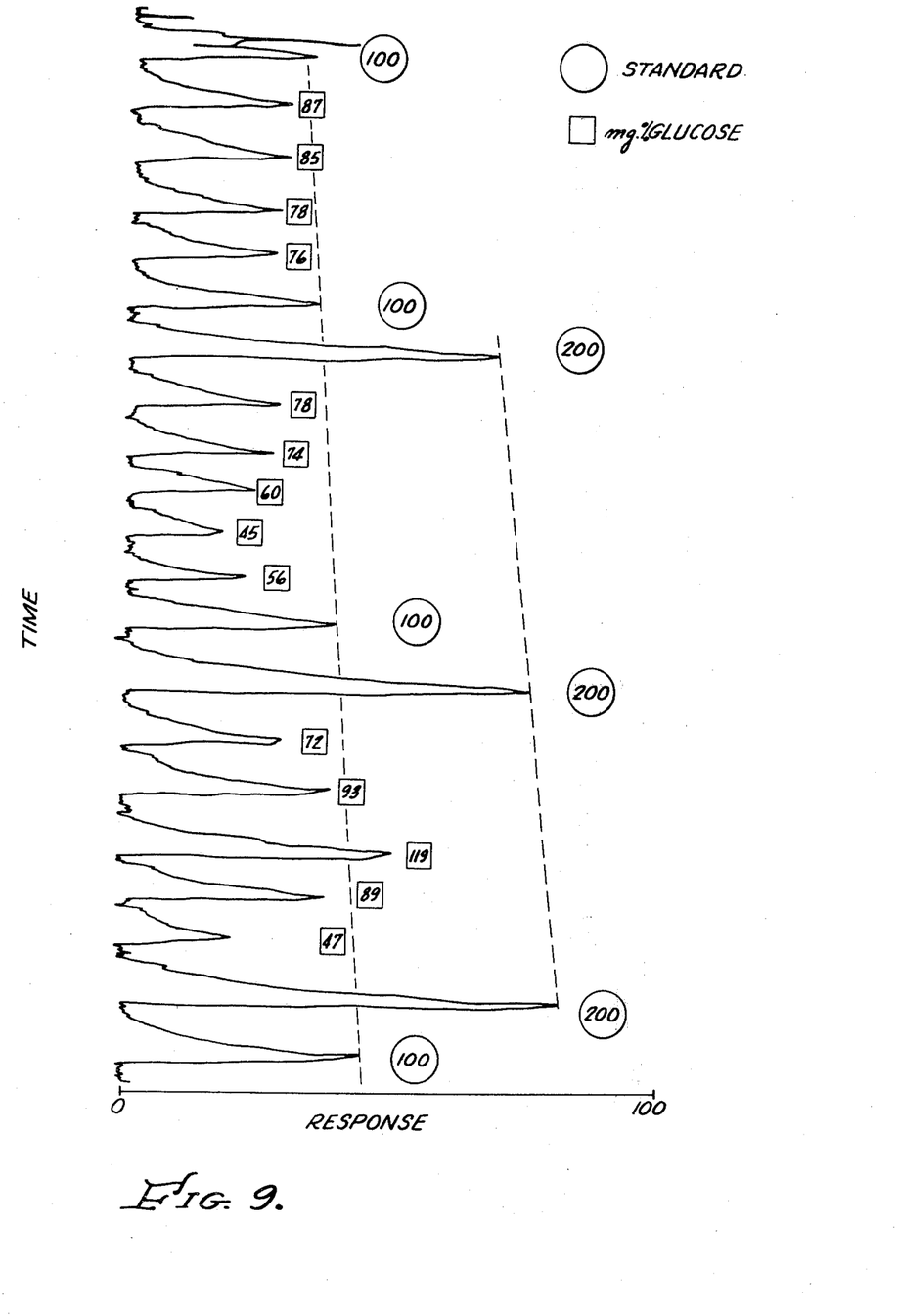
FIG. 9 is a set of typical recorder data for a multiple sample run in a single beaker of enzyme.

The following are specific examples of glucose determination in blood and urine made with the apparatus shown in FIGS. 2 and 6, with an anode voltage supply of +0,8 volts and having an electrical RC time constant of 2.5 seconds employing a 25 K ohm resistor and a 100 μfd capacitor:

EXAMPLE 2 — SINGLE BATCH OF ENZYME-MULTIPLE BLOOD GLUCOSE DETERMINATION a. Enzyme Solution — an enzyme preparation was made by diluting 1500 units/ml activity Ovazyme XX glucose oxidase (Fermco Division of G. D. Searle Co.) with about two parts of buffered solution containing iodide, iodine and ammonium molybdate to give a preparation having an enzyme activity of 500 units/ml containing 0.01 M KI, 0.005 M ammonium molybdate and 50 mg. of iodine per liter. The pH is adjusted to 5.9 with solid sodium acetate in some runs and to 7.0 with dibasic sodium or potassium phosphate in other runs.

b. A single batch of 10 ml of enzyme solution is placed in an open 30 ml beaker and stirred at 10 rps to saturate the solution with oxygen. The oxygen sensor is inserted into the beaker and equilibrated before a 100 or 200 mg percent portion of glucose is added and the meter calibrated to 100 percent full scale response.

c. A 100 μl sample of centrifuged blood serum or plasma samples without deproteinization is added to the stirred enzyme solution and the rate curve increases to a peak response, then decreases and actually passes through zero to give a rate of increase of oxygen level in the solution due to stirring replenishing oxygen. Recovery to zero baseline is not necessary and the successive samples can be injected when the minimum signal from the preceding sample is reached. Calibration samples are interspersed about every 5 samples. The results of a run as recorded on the recorder are shown in FIG. 9.

Reading from right to left, the first two peaks represent a 100 mg percent and 200 mg percent glucose calibration as shown in the circles. The first 100 µl sample of blood serum was added after recovery of the instrument 0 to minimum signal and the recorder pen deflection increased sharply to a peak response which corresponds to 23.5 percent of the 200 mg percent calibration or 47 mg percent of glucose as shown in a square above the peak. The succeeding sample responses in mg percent are each displaced in squares and the calibration responses in circles. The continuously downward drifting 100 percent requires connection of calibration points with the lines and calculation of results as ratios of peak heights to tie line at peak time.

The enzyme can be used repeatedly for 60 or more determinations provided sufficient calibration samples are interspersed to correct for the approximate 3 percent decrease in response with each re-use due to dilution. Replacement of 1.5 cc of enzyme solution by 1 cc of fresh enzyme after every fifth sample holds the calibration drift to approximately 30 percent over 60 samples with standard deviations of only ±2 percent found despite the slight drift within each set of five samples. With this replacement procedure, calibration standards need only be inserted about every tenth sample. Actual operating time, including set-up, calibration, and calculation of results averaged less than 3 min/sample for the single batch enzyme procedure.

In a clinical evaluation of 265 blood samples, replicate determinations were made by the above procedure, by the Folin-Wu method and by spectrophotometric determination of the color change due to reaction of ferricyanide with glucose. The internal consistency of the batch analyzer when operated by one who has developed experience and proficiency corresponds to an overall standard deviation of o = to about ±2 percent of reading. These results may be compared with the internal consistency of the spectrophotometric analyzer which is ±4 percent. Comparison with Folin-Wu values gave Folin-Wu values on the average 10 mg percent above the batch analyzer values which is expected when comparing a specific glucose assay with a total reducing substance method.

While it has been demonstrated that good data can be consistently obtained by the single enzyme batch procedure, the non-absolute nature of the instrument zero and the downward drifting 100% line which requires repeated calibration limits somewhat the attractiveness of the procedure.

It has been found that the procedure is substantially simplified by using fresh enzyme in individual sample cups. Each sample starts from a zero level which represents a steady oxygen signal in an air pre-saturated sample cup, and the enzyme and substrate concentrations are the same in all of the sample cups for equivalent sample volumes. Use of the equipment as described in FIG. 6 makes the running of successive samples simple and convenient. Samples can still be run at a repetition rate of two to three minutes per sample according to the following procedure.

EXAMPLE 3 INDIVIDUAL ENZYME SAMPLE CUP PROCEDURE a. Three ml of the enzyme solution of Example 2 (a) are placed in each cup.

b. Calibration of instrument by a 100 µl run of a 100 mg percent glucose sample.

c. Each sample containing a ⅛ inch D, ½ inch long magnetic stirring bar is placed over the stirring motor, the polarographic sensor lowered into identical position and the solution stirred until the sensor equilibrates. 100 µl samples of blood serum are then added and the rate is recorded through maximum peak response which is read directly from the meter or recorder pen deflection. The peak responses are as sharp and as definite as those of FIG. 9 from the single enzyme procedure and on recalibration after ten serum samples the calibration peak was substantially identical to that of the original calibration.

A procedure similar to the glucose assay method can be utilized for determining glucose oxidase activity. The dependence of reaction rate upon enzyme activity or concentration can be evaluated on a proper basis of concentration per unit time according to the following relationships:

$$i_{Derivative} = RC \frac{di_S}{dt} = -kC \frac{d(O_2)}{dt}$$

where $i_s$ is the sensor current and R and C are the differentiating resistor and capacitor.

$$i_s = k(O_2)$$

$$i_{so} = k(O_2)_o = k \cdot S \; ; \; K = \frac{i_{so}}{S}$$

where S is the oxygen solubility and the subscript "o" denotes initial conditions for air-saturated solution. Hence, $$-\frac{d(O_2)}{dt} = \frac{60 i_{Derivative} \cdot S}{RC \cdot i_{so} \cdot G_o} = K \cdot E = 2 \times 10^{-3} \text{min.}^{-1} \cdot E$$

from which $$E = \frac{30000 \, i_D \cdot S}{RC \cdot i_{so} \cdot G_o}$$

The glucose activity assay procedure differs in that the solution in the beaker contains an excess of glucose as contrasted to an excess of glucose oxidase in the glucose assay procedures. The amount of glucose, however, is insufficient to deplete the dissolved oxygen before maximum rate is reached. The use of small enzyme samples in larger volumes of buffered glucose eliminates the effect of salt content of the enzyme sample on the results. The following is an example of the glucose oxidase assay method of the invention utilizing the apparatus disclosed in FIG. 2. and FIG. 6.

EXAMPLE 4 — 4 GLUCOSE OXIDASE ACTIVITY ASSAY

A reagent solution is prepared containing 30 mg percent glucose, 0.2 M acetate buffer (pH 6.0), 0.01 M KI, 50 mg iodine per liter, 5 percent ethanol, and 0.005 M ammonium molybdate. Three ml of this solution are introduced into a sample cup. The oxygen sensor is allowed to equilibrate with the stirred solution, and a sample of 20µl, of 1500 units per ml glucose oxidase solution is introduced into the cup. The meter is set to give a full scale response.

A 20 µl sample of unknown activity glucose oxidase enzyme solution is added to a sample cup containing 3 ml of stirred reagent solution and the peak response corresponding to maximum rate is recorded and is proportional to the activity of the standard calibration peak response.

Figure 10:
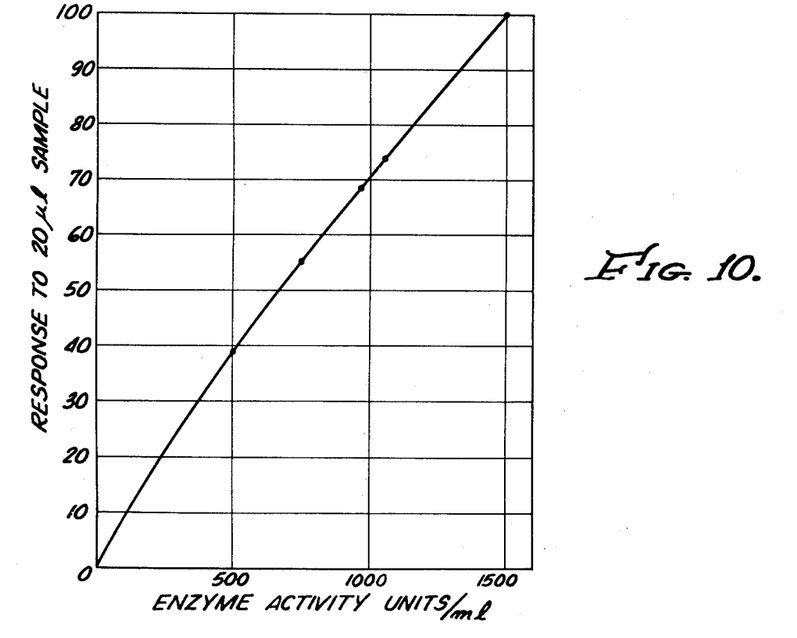
FIG. 10 is a graph illustrating the near linearity of enzyme assay.

If the glucose oxidase sample is of very low activity, a calibration curve of activity versus volume is prepared from various dilutions of the known sample or by using 10 and 20 µl samples of the 1500 units ml standard. The slight non-linearity is adequately covered by two calibration points as shown in FIG. 10. 50 and 100 µl samples may now be run and the response is multiplied by 20 over 50 or 100 to give the enzyme activity in units/ml or activity corresponding to the dilution is read from the calibration curve. With calibration, an enzyme assay may require 15 minutes. If the calibration has already been done, an individual assay will require about 2 minutes.

As previously discussed, the freedom of interference of the glucose oxidase (G.O.) glucose-oxygen method finds its most striking demonstration in the applicability to urine samples without preliminary treatment of the urine. In fact, it has been previously reported by Salomon, et al, Anal. Chem. 31, 453 (1959) that the glucose oxidase method cannot be applied directly to urine. This resulted from confusion between the primary G.O. reaction and the secondary peroxidase oxidation of a chromogen with which the G.O. reaction is usually coupled.

The batch glucose monitor provides a better true glucose value than the spectrophotometric method employing peroxidase and a chromogen. It is still surprising to find that urine samples can be introduced directly into the G.O. enzyme reagent without performing any preliminary operations.

The procedure is essentially similar to that of Examples 2 and 3. Urine which is normally deficient in oxygen is aerated by pre-stirring for a period of time, or by shaking a sample of the urine in a test tube or bottle. Best results are obtained by using a small polyethylene bottle for aerating. After shaking an approximately half full bottle, the cap is opened, and the bottle is squeezed gently to drive out the oxygen-depleted air; the bottle squeezing is released to admit fresh air, and the bottle is capped and shaken again. A few repetitions of this procedure insures complete aeration. The instrument is calibrated at the 100 mg percent glucose level but the sample size is 200 µl to allow for lower glucose levels found in normal urine.

The following is an example of batch glucose urine assay for normal subjects again utilizing the instrument described in FIGS. 2 and 6.

EXAMPLE 5 — BATCH URINE GLUCOSE ASSAY a. Enzyme solution preparation. The glucose oxidase enzyme solution of Example 2(a) is utilized.

b. Three ml of enzyme solution are placed in a series of sample cups stirred at 10 rps. The instrument is calibrated to give full scale response for 100 mg percent glucose.

c. The cup of enzyme solution is placed over the magnetic stirrer and after the sensor equilibrates, 200 µl samples of urine are introduced and the peak response is noted and recorded. The glucose content of the sample is determined from the ratio of the peak response to that of the standard. Again, these results are obtained within about a period of 2–3 minutes per sample.

Meaningful data are obtained in the range of 5 mg percent up to 100 mg percent glucose within ±2 mg percent. The 100 mg percent level has previously been considered trace. Since values in this range can now be measured, it is possible that diagnosis of emerging conditions can be made much earlier and without requiring a venipuncture.

If significant glucose is present in the urine, dilution of the urine may be necessary. For example, with a poorly controlled diabetic subject, it was necessary to dilute the urine 40:1 with distilled water before running the sample on the instrument set up as for normal blood samples (with approximately 200 mg percent reading full scale); the sample was found to contain 4.8 gms of glucose per 100 milliliters of urine. It is most important to note, however, that no preliminary clean-up of the urine is required before it can be run in the batch glucose monitor. In addition, full normal response to glucose standards has been found in enzyme already contaminated by the addition of 200 microliters of urine; in fact, as a check procedure, standards were run after reestablishment of baseline in the cups to which the urine sample had already been introduced, with no adverse effects found.

In one set of urine runs, the batch of enzyme had an appreciable iodine color before sample introduction. The iodine was bleached by the urine samples in differing times but was shown to be without influence on the oxygen sensing batch glucose monitor of the invention, whereas the iodine-reducing substances seriously interfere with the peroxide-peroxidase-chromogen portion of the usual colometric prior art procedures.

It is to be understood that the foregoing disclosure relates only to preferred embodiments of the invention and that numerous modifications or alterations are possible.

what is claimed is:

1. A method of determining the concentration or activity of a material present in a sample which is chemically reacted in batch comprising:
    monitoring a property or characteristic of a component or product of said reaction related to concentration of a substance in said batch;
    generating a first electrical signal related to said concentration of said substance;
    differentiating said first signal to obtain an output signal proportional to the instantaneous time rate of change of concentration of said substance; and
    measuring said output signal to determine the concentration or activity of said material.

2. The method according to claim 1 wherein said measuring step includes measuring a maximum of said output signal.

3. The method according to claim 2 wherein said output signal is generated continuously.

4. A method of determining the glucose concentration of a sample comprising the steps of:
    oxidizing the glucose present in the sample in an oxygen saturated aqueous solution by means of glucose oxidase in the presence of a sensor which serves to monitor a property or characteristic of oxygen in said solution related to the oxygen concentration thereof:

generating a first electrical signal related to said oxygen concentration;
differentiating said first electrical signal to produce an output signal proportional to the instantaneous time rate of change of oxygen concentration; and
measuring a maximum of said output signal to determine said glucose concentration.

5. A method of determining the glucose concentration of blood or urine samples comprising the steps of:
stirring at constant speed a fixed volume of an oxygen saturated solution of buffered glucose oxidase in the presence of an oxygen sensor until the sensor equilibrates with the solution, said sensor serving to monitor a property or characteristic of oxygen in said solution related to the oxygen concentration therein;
adding a measured amount of sample to the solution and reacting the glucose with oxygen while stirring at a substantially constant speed;
generating a first electrical signal related to said oxygen concentration;
differentiating said first signal to produce a second signal proportional to the instantaneous time rate of change of said oxygen concentration;
recording said second signal; and
determining said glucose concentration from a maximum of said second signal.

6. A method according to claim 5 in which the buffered glucose oxidase solution contains iodine, and iodine and molybdate ions to inhibit bacteria and to suppress formation of oxygen by peroxide decomposition.

7. A method according to claim 6 in which the glucose oxidase solution contains 0.01 M KI, 0.005 M ammonium molybdate, 50 mg. of iodine per liter, 5 percent ethanol and buffer salts to control the pH in the range from 4.5 to 8.0.

8. A method according to claim 7 in which the buffer salts are selected from alkaline metal acetates and dibasic phosphates and are present in sufficient amounts to adjust the pH to about 5.6 to 7.5.

9. A method according to claim 6 in which the glucose oxidase solution contains 5 percent ethanol.

10. A method according to claim 5 in which the solution is stirred at a constant speed less than 12 rps.

11. A method according to claim 10 in which the stirring speed is from about 5 to 10 rps.

12. A method according to claim 11 in which the solution volume is up to 10 ml.

13. A method according to claim 5 in which glucose content of blood serum or plasma in the range of 25 to 250 mg percent is determined.

14. A method according to claim 13 in which the sample size is from 10 to 100 $\mu$l.

15. A method according to claim 14 in which the red cells of the sample are removed by centrifugation before the glucose determination.

16. A method according to claim 5 in which the reaction is conducted at constant temperature.

17. A method according to claim 16 in which the reaction is conducted at a constant temperature within the range of 15°C to 60°C.

18. A method according to claim 5 in which the glucose content of urine is determined.

19. A method according to claim 18 in which the urine sample is pre-aerated and added to the glucose oxidase solution without preliminary purification.

20. A method according to claim 5 in which the oxygen sensor is a polarographic sensor containing a KCl cathode, a silver anode, and KCl electrolyte and a permeable one mil polytetrafluoroethylene membrane.

21. A method according to claim 20 in which the membrane is stretched to show the whitening charcteristic of crystallization.

22. A method according to claim 5 in which the volume of enzyme solution is no less than about 3 ml for a 100 $\mu$l sample containing up to 400 mg percent glucose.

23. A method according to claim 5 in which the glucose oxidase solution is pre-aerated.

24. A method according to claim 5 in which the glucose oxidase activity is from to 200 to 750 units per ml.

25. A method according to claim 5 in which a plurality of determinations are run from the same batch of buffered glucose oxidase.

26. A method according to claim 5 in which a plurality of glucose determinations are consecutively run, utilizing a fixed volume of fresh glucose oxidase for each sample.

27. A method of directly determining the activity of an enzyme comprising:
reacting said enzyme with an excess of substrate;
monitoring a property or characteristic of a component or product of the reaction related to concentration of a substance therein and generating a first electrical signal related to said concentration;
differentiating said first electrical signal to produce an output signal proportional to the instantaneous time rate of change of said concentration; and
measuring said output signal to determine the activity of said enzyme.

28. A method according to claim 27 wherein said step of measuring includes measuring a maximum of said output signal.

29. A method of determining the catalase activity of samples of body tissue homogenates and body fluids comprising:
reacting a measured portion of a catalase-containing sample with a fixed quantity of a stirred buffered peroxide solution as substrate;
stirring the solution and sample at a constant rate in the presence of an oxygen sensor;
generating a first electrical signal related to the dissolved oxygen concentration;
differentiating said first electrical signal to produce a second electrical signal proportional to the instantaneous time rate of change of oxygen concentration; and
measuring said second electrical signal to determine said catalase activity.

30. A method according to claim 29 in which the peroxide solution contains hydrogen peroxide of from about 0.006 M to 0.4 M and alkali metal phosphate buffer of from 0.025 M to 0.1 M.

31. A method according to claim 30 in which 100 to 200 $\mu$l of a catalase-containing sample are added to 10 ml of 0.006 M $H_2O_2$ in a 0.25 M phosphate buffer at pH of about 7.

32. A method according to claim 30 in which 1 ml of 10 percent tissue homogenate is added to 30 ml of 0.4 M hydrogen peroxide in pH phosphate buffer.

33. The method according to claim 29 wherein the step of measuring includes measuring a maximum of said output signal.

34. The method according to claim 29 wherein said output signal is generated continuously.

35. A method of determining the concentration or activity of an oxygen producing or consuming component of a reaction catalyzed by a reagent containing an enzyme selected from the group consisting of oxygenases, hydrogenases, reductases, hydroxylases and oxidases comprising:

conducting the reaction of the reagent and component in batch;

monitoring a property or characteristic of oxygen in said reaction related to the oxygen concentration therein and generating a first electrical signal related to said oxygen concentration;

differentiating said first electrical signal to produce an output signal proportional to the instantaneous time rate of change of said oxygen concentration; and measuring said output signal to determine the concentration or activity of said oxygen producing or consuming component.

36. A method according to claim 35 in which the reagent is oxygen stable.

37. A method according to claim 36 in which component is glucose, said enzyme is glucose oxidase and said reagent contains a catalase and a sufficient amount of ethanol to consume hydrogen peroxide in the reaction mixture without liberating oxygen.

38. A method according to claim 37 in which said reagent contains iodine and molybdate ions in sufficient amounts to suppress formation of oxygen by hydrogen peroxide decomposition.

39. A method according to claim 37 in which said reagent contains about 5% ethanol.

40. A method according to claim 37 in which said reagent has a glucose oxidase activity of from 200 to 750 units per ml.

41. A method according to claim 36 in which said reagent contains a natural impurity which is capable of converting hydrogen peroxide to oxygen, and a constituent which consumes hydrogen peroxide in the presence of said impurity without liberating oxygen.

42. A method according to claim 41 in which said impurity is catalase.

43. A method according to claim 42 in which said reagent has sufficient enzyme activity to cause at least 75 percent completion of said reaction within about one minute.

44. A method according to claim 36 in which said reagent has sufficient enzyme activity to cause at least 75 percent completion of said reaction within about one minute.

45. The method according to claim 35 wherein the step of measuring includes measuring a maximum of said output signal.

46. The method according to claim 35 wherein said output signal is generated continuously.

* * * * *

UNITED STATES PATENT OFFICE
CERTIFICATE OF CORRECTION

Patent No. 3,933,593　　　　　　　　　　Dated　January 20, 1976

Inventor(s)　James C. Sternberg

It is certified that error appears in the above-identified patent and that said Letters Patent are hereby corrected as shown below:

Column 8, line 42, delete "an" and substitute --and--.

Column 12, line 12, delete "10-7" and substitute --$10^{-7}$--

Column 16, line 28, delete the following equation:

$$i_{Derivative} = RC\frac{di_s}{dt} = -kC\frac{d(O_2)}{dt}$$

and substitute the following equation:

$$i_{Derivative} = RC\frac{di_s}{dt} = -kRC\frac{d(O_2)}{dt}$$

Signed and Sealed this twentieth Day of April 1976

[SEAL]

Attest:

RUTH C. MASON　　　　　　　　　　C. MARSHALL DANN
Attesting Officer　　　　　　　　Commissioner of Patents and Trademarks